United States Patent
Stiller et al.

(10) Patent No.: US 6,813,961 B2
(45) Date of Patent: Nov. 9, 2004

(54) METHOD AND APPARATUS FOR THE TESTING OF CUBOID-SHAPED PACKS

(75) Inventors: Martin Stiller, Verden (DE); Jens Schmidt, Grasberg (DE); Ralph Sgodzai, Ritterhude (DE); Henry Buse, Visselhövede (DE)

(73) Assignee: Focke & Co. (GmbH & Co.), Verden (DE)

( * ) Notice: Subject to any disclaimer, the term of this patent is extended or adjusted under 35 U.S.C. 154(b) by 353 days.

(21) Appl. No.: 09/973,534

(22) Filed: Oct. 9, 2001

(65) Prior Publication Data

US 2002/0069705 A1 Jun. 13, 2002

(51) Int. Cl.⁷ ................................................ G01N 3/08
(52) U.S. Cl. ............................................................ 73/818
(58) Field of Search .......................... 73/818, 821, 823, 73/824, 825, 865.8; 53/53

(56) References Cited

U.S. PATENT DOCUMENTS

| | | |
|---|---|---|
| 4,916,883 A | 4/1990 | Focke |
| 4,984,409 A * | 1/1991 | Focke ............................ 53/53 |
| 5,209,124 A * | 5/1993 | Graudejus et al. ............ 73/821 |
| 6,202,476 B1 * | 3/2001 | Fenlon ........................ 73/49.3 |

FOREIGN PATENT DOCUMENTS

| | | |
|---|---|---|
| DE | 69303010 T2 | 9/1993 |
| DE | 19614475 A1 | 10/1997 |
| DE | 19917457 A1 | 10/2000 |
| EP | 0 195 173 A1 | 9/1986 |
| EP | 0 360 693 A1 | 3/1990 |

* cited by examiner

*Primary Examiner*—Edward Lefkowitz
*Assistant Examiner*—Corey D. Mack
(74) *Attorney, Agent, or Firm*—Technoprop Colton LLC

(57) ABSTRACT

For acquiring characteristic data of a pack (10), in particular of a cigarette pack, the latter is compressed between a pressure plate (26) and a bearing plate (27). The latter is connected to a load cell (28) in order to determine the applied force as a function of the distance traveled. The characteristic deformation data or change in force at a precise, constant downward movement of the pressure plate (26) yield a reproducible, characteristic image of the pack (10) in question.

27 Claims, 4 Drawing Sheets

METHOD AND APPARATUS FOR THE TESTING OF CUBOID-SHAPED PACKS

BACKGROUND OF THE INVENTION

The invention relates to a method for the testing of packs of formable packaging material, especially of (cigarette) packs having at least one wrapper of (thin) cardboard. The invention also relates to an apparatus for implementing the method.

BRIEF SUMMARY OF THE INVENTION

The testing of packs is particularly important in the manufacture of cigarette packs, which requires a high degree of precision.

The invention is based on the problem of suggesting measures for implementing a precise testing of packs which can also be executed in a simple manner.

For solving this problem, the method according to the invention is characterized in that the pack is impinged by a defined or measured pressure, giving rise to deformations which are then measured and evaluated.

Essential to the invention is the knowledge that the progression of the deformation caused by pressure on the pack is characteristic for its construction and also for its contents. Furthermore, certain features of its construction and design can be identified by its deformation curve.

According to the invention, the course of pack deformation is determined by changes in the force applied for deformation with respect to a preset default deformation curve. In actual practice this means that a pressure-exerting means acting on the pack is measured with respect to the distance covered and the force occurring during the deformation process. The measured results are recorded and evaluated on a continual basis, in particular by graphic representation. This result of evaluation is displayed on a computer as a curve plotting the variables of force and distance. The pressure-exerting means is preferably pressed against or set upon the pack with uniform, in particular, constant movement. The force resulting from the pack's resistance is measured and plotted over the distance.

One special feature of the invention ties it the knowledge that, during the deformation process, a change in the measured force occurs a number of times, specifically as a result of the pack's structural details. In an advantageous exemplary embodiment, namely when testing a cigarette pack of the hinge-lid type, the force applied during the deformation process is recognizably influenced by structural details such as lid inner tabs, transverse edges at the lid end as well as at the bottom end, generating in the graphic recording of the force curve a typical and reproducible image of the deformation behavior of the pack.

The recorded and graphically displayed results of measurement can, according to the invention, be compared with a reference curve or a stored "calibration curve" in order to identify any deviations from a standard embodiment of the pack concerned. One special feature lies in the fact that for this purpose the second derivative of the force/distance curve is determined and recorded. The resulting curve exhibits elevated curves or peaks which correspond to an increased force or increased pack resistance to deformation, thus enabling one to draw conclusions concerning the construction as well as the material composition, material strength and the pack contents.

The present measuring and testing method can be applied with particular advantages to cigarette packs of the hinge-lid type, i.e. to a pack made of thin cardboard. The pack is tested after it is finished, either before or after it is surrounded by an outer wrapper of film.

For implementing the method according to the invention, the pack is clamped as a whole between pressure-exerting means which are displaceable relative to one another, namely in particular between an (upper) pressure plate and a (lower) plate-shaped load cell. At least one means is displaceable. The path traveled is measured as well as the attending force. This yields the characteristic deformation behavior of the pack.

Method and apparatus can be integrated in a packaging process, preferably by positioning a test station in the region of a pack conveyor, with pack samples being removed from the conveying stream and tested for their correct shape.

Further special features of the invention are explained below in more detail by means of an exemplary embodiment of an apparatus and by means of the evaluation procedure. Shown are:

DETAILED DESCRIPTION OF THE PREFERRED EMBODIMENTS

Figure 1:
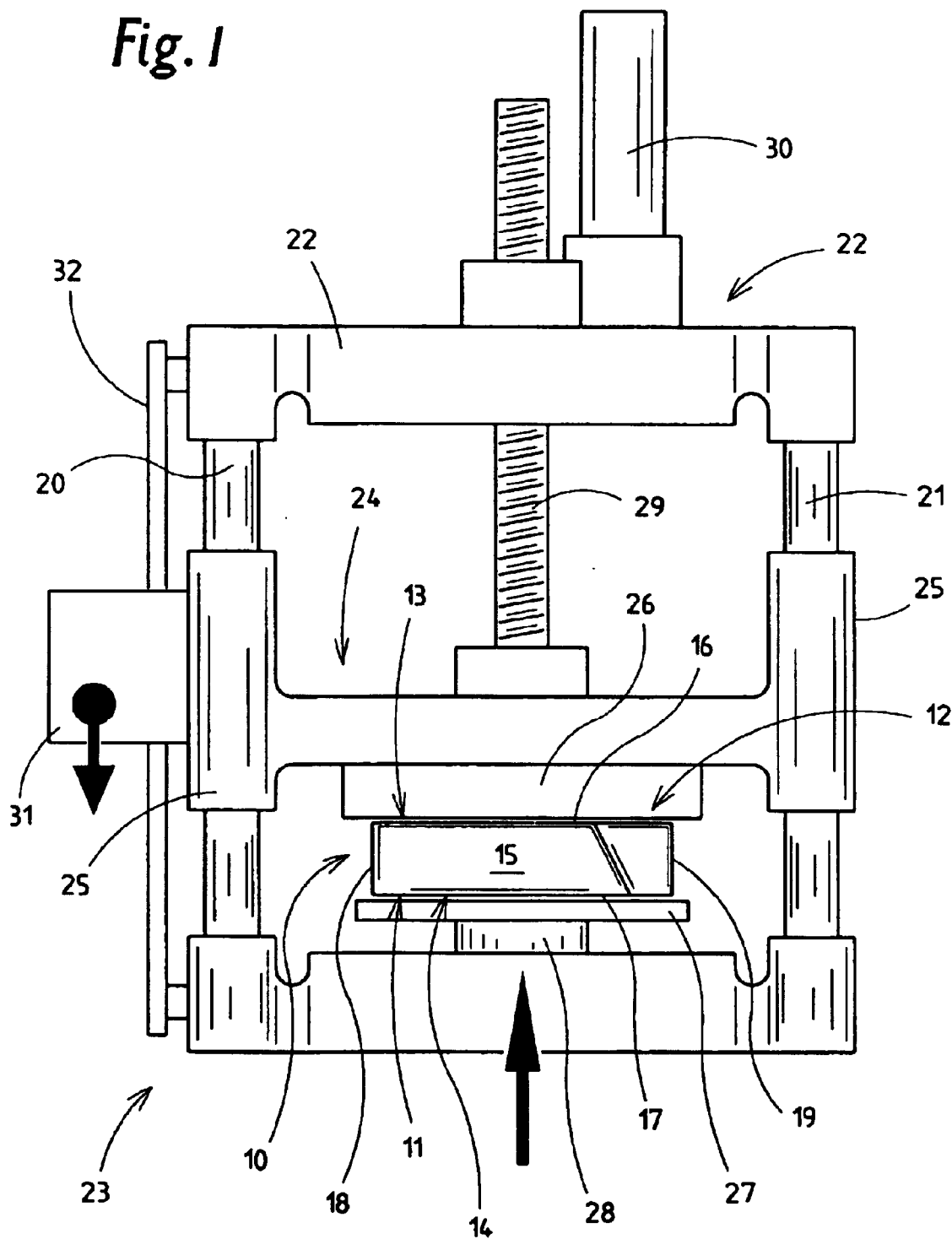
FIG. 1 side view of an apparatus for testing a pack.

The following described details relate to the preferred field of application: the testing of packs 10, namely of cigarette packs, specifically those of the hinge-lid type. This type of pack 10 is made of thin cardboard. The pack comprises a (lower) box part 11 and a lid 12 hinged thereto. The pack 10 has a rectangular cubical shape with a large-surface front side 13 and corresponding rear side 14. Box part 11 and lid 12 form elongate, double-layered side walls 15. The blank for the pack 10 is folded such that the pack sides or walls are delimited by (upright) right-angled pack edges 16, 17 and transverse edges 18, 19.

The pack 10 is tested in a variety of ways with the help of exerted pressure or compressive strain. To this end the pack 10 is positioned between pressure-exerting means which abut the cubed-shaped pack 10 in the region of its large-surface pack sides, namely in the region of front side 13 and rear side 14. As a result of the (downward) movement of at least one pressure-exerting means, pressure is applied to the pack 10, thus inducing its deformation. Relevant features concerning the material of the pack (10) and its constructive design can be derived from this.

The testing device shown in FIG. 1 comprises (upright) supporting columns 20, 21. These are connected to each other at their (upper and lower) ends by means of transverse traverses 22, 23 to form a supporting framework. A pressure-exerting means can be displaced between the traverses 22, 23, namely a pressure strut 24, which can be displaced with slide bushes 25 along the supporting columns 20, 21. The pressure strut 24 carries the pressure-exerting means, namely a pressure plate 26. The latter abuts the top or front side 13 of the pack 10 in order to apply pressure.

A bearing plate 27 below the pack 10 serves as a counterpressure piece. This bearing plate 27 is connected to a pressure gauge, which in the present case is a load cell 28. This is a device, commonly known in the trade, which can measure the transferred pressure and convert it into electric signals, particularly by means of a wire strain gauge. Accordingly, the load cell 28 measures the pressure applied to the pack 10 during the uniform, in particular continual, downward movement of the pressure plate 26.

The pressure-exerting means, namely pressure plate 26 and bearing plate 27 have a bearing surface for the pack 10 which is larger than the latter, or than front side 13 and rear side 14. The pack 10 is therefore impinged by the pressure-exerting means over its entire surface.

The apparatus is configured such that the (lower) bearing plate 27 is stationary and the pressure plate 26 for transferring pressure can be lowered onto the pack 10. For this purpose, the pressure strut 24 can be lifted and lowered by a linkage mechanism, in the present case by a worn gear with an upright spindle 29 rotatably mounted in the upper is traverse. A rotatable spindle nut is driven by a motor, namely by an electric motor 30. The (spindle) drive thus moves the pressure plate 26 in a predetermined, in particular continuous, conveying movement against the pack 10, specifically by means of the pressure strut. During its deformation or compression, the pack generates resistance, which is measured by the bearing plate or load cell 28.

The movement of the pressure-exerting means or of the pressure plate 26, on one hand, and the force occurring during the deformation of the pack 10 are measured and recorded. To this end, the pressure plate 26 or the pressure strut 24 is assigned to a position sensor 31 of known make. The position sensor 31, which can be moved up and down along an upright guide rod 32 attached to the side of the apparatus, makes a precise measurement of the distance traveled and converts it into electric signals.

One special features lies in the fact that the measured data variables, distance and force, are displayed graphically. The data are processed by computer and displayed as a graphic image, namely as a curve. The measured force is plotted along the y-axis and the distance covered is plotted along the x-axis.

Figure 2:
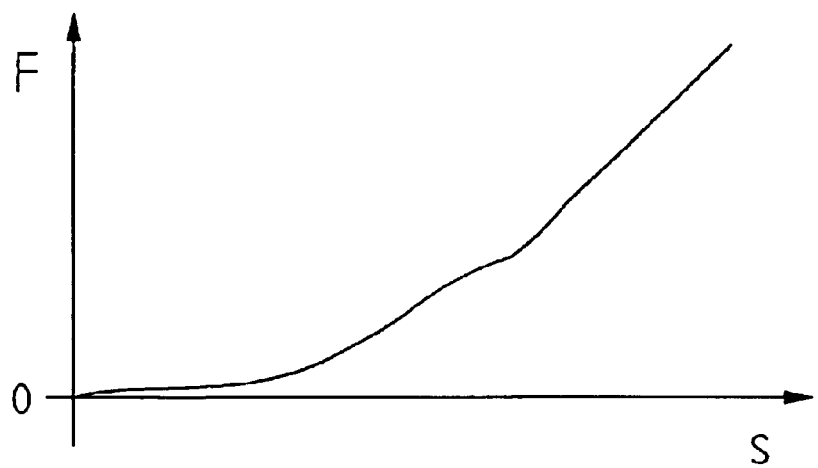
FIG. 2 is a graph representing the deformation of a pack and showing the curve on the basis of direct interaction between force F and distance S.

FIG. 2 shows the curve on the basis of direct interaction between force F and distance S. The curve commences at the point of contact with the pack 10 by the bearing plate 27 and continues up to the point where the pack is deformed without being destroyed, in particular up to the point where compression of the cigarettes begins.

Figure 3:
FIG. 3 is a graph representing the deformation of a pack and showing a curve which has been calculated as the first derivative of the curve shown in FIG. 2.
Figure 4:
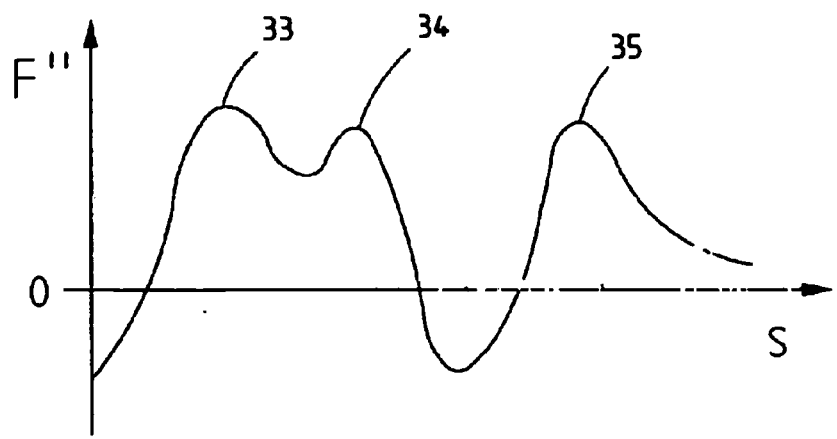
FIG. 4 is a graph representing the deformation of a pack and showing a curve which has been calculated as the second derivative of the curve shown in FIG. 2.

FIG. 3 shows a curve which has been calculated as the first derivative of the curve shown in FIG. 2. However, a favorable representation of the pack 10 with respect to its behavior during compression is shown in FIG. 4, namely the second derivative of the described interaction. The curve displays a number of crests 33, 34, 35, namely peaks, which each represent an increase of pressure resulting from the construction of the pack 10, namely for an altered or increased compressive strength exerted by the pack 10 during the constant downward movement of the pressure-exerting means.

The curve in FIG. 4 shows properties of a pack 10 of the hinge-lid type (FIG. 1). The curve begins when the pressure plate 26 is set upon the top side, namely the front side 13 of the pack 10. The first curve peak 33 can be attributed to an increase in force by a lid inner tab common to hinge-lid packs, i.e. to a material reinforcement in the region of the upward-directed lid front wall.

The following curve peak 34 can be attributed to a further increase in resistance during the deformation of the pack 10 and to a increase in force resulting therefrom, namely to an increased stiffness in the region of the lid 12. The transverse edges 19 at the end or corner increase the resistance of the pack 10, thus causing an increased deformation force.

Following this, namely during the continued pressure-exerting movement of the pressure plate 26, there is again a new peak or rise in the curve 35 by a corresponding reaction of the pack 10. This rise in force is caused by the stiffness of the pack due to the traverse edges 18 at its bottom side. Immediately afterwards, the process of compressing the pack 10 is completed. This results in an overall curve according to FIG. 4 which is characteristic for a certain pack type, in the present case for a hinge-lid box.

Another special feature now lies in the fact that the method can be employed in various ways, specifically for identifying correct or faulty packs. Here the knowledge is kept in mind that material strength, for example the thickness of the cardboard, the type and nature of an innerliner, the type, nature and formation of the cigarette group and other characteristics in the pack construction have an influence on the curve resulting from the application of pressure during the testing procedure.

During the testing of packs, special attention is given to comparing the curve recorded during testing, in particular the curved obtained from the second derivative, against one or more stored reference curves. This may involve a "calibration curve" for correct, standard packs of the type to be produced. Faulty packs can be identified with the help of this testing method.

Figure 5:
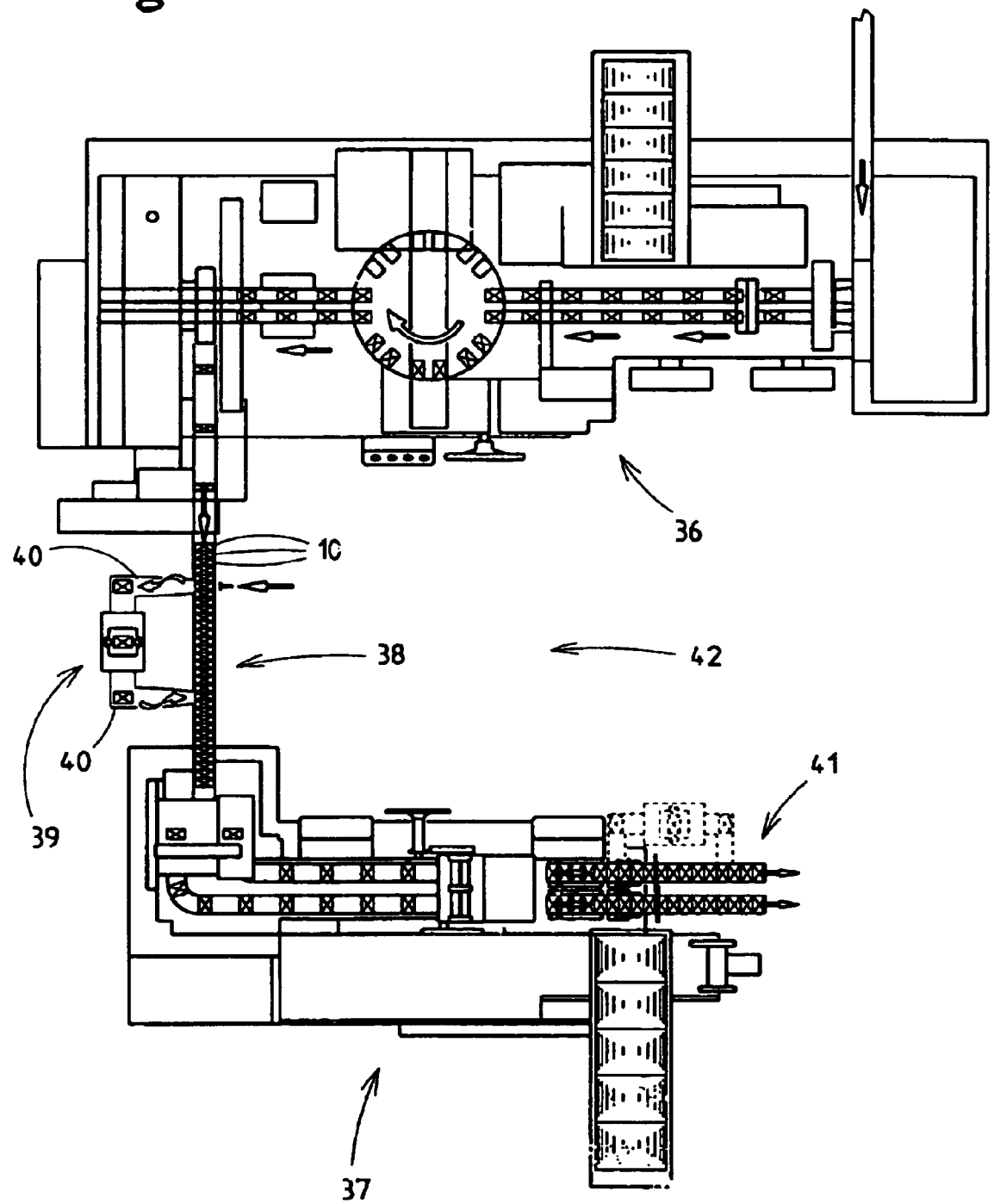
FIG. 5 a machine unit for manufacturing cigarette packs, in schematic plan view, FIG. 6 installation comprising a plurality of machine units, also in schematic plan view.
Figure 6:
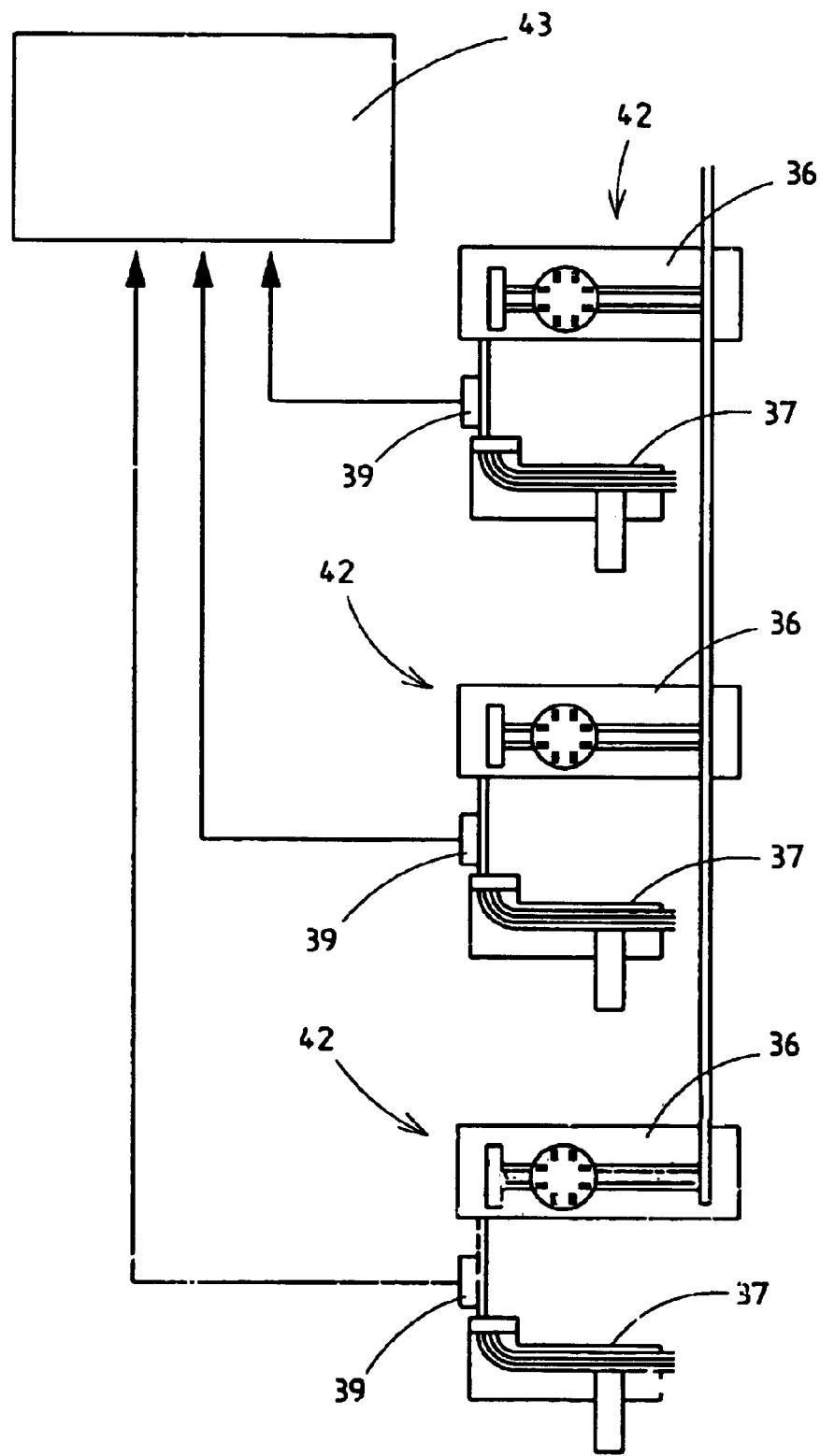

Another special feature lies in integrating the testing method or a testing apparatus, for example within the meaning of FIG. 1, in the production flow of the packs 10. FIG. 5 shows the layout of a packaging unit for hinge-lid packs. The unit comprises a packaging machine, or packer 36, and a packaging machine for the production of an outer cellophane wrapper, a so-called cello-packer 37. The two packaging machine are connected to each other by a straight-line pack conveyor 38. A test station 39 is arranged in the region of this conveying path. Individual packs 10 are moved out of the region of the pack conveyor 38 at random for testing and conveyed through the test apparatus pursuant to FIG. 1. The tested pack is then fed back to the pack conveyor 38 by the intermediate conveyor 40. It is advisable to test the packs 10 in cycles. In addition or as an alternative, the test station 39 can also be positioned at the end of the cello-packer 37, for example in the region of the pack paths 41 downstream of the cello-packer 37.

The testing of the packs 10 can be conducted for a complete installation comprising a plurality of packaging units pursuant to FIG. 5. Each of the test stations 39 is provided with a computer and preferably a monitor for displaying the curves pursuant to FIG. 2 to FIG. 4. In addition or as an alternative, the test stations 39 of the packaging units 42 are connected to a central computer 43, which logs the operational data. In this way, is it possible to establish a central store of information and test results for an entire packaging installation.

With the testing method it is possible to draw conclusions concerning any sources of error. These may lie in the pack or packaging material itself, or may also be found in an operation of the packaging machine. Conclusions to this effect can be drawn on the basis of the characteristics of the measured values or of the plotted curve. Furthermore, it is possible to draw conclusion concerning machine wear on the basis of a gradual change in pack behavior during testing.

List of designations 10 pack
11 box part
12 lid
13 front side
14 rear side
15 side wall
16 pack edge
17 pack edge
18 transverse edge
19 transverse edge
20 supporting column
21 supporting column
22 transverse
23 transverse
24 pressure strut
25 slide bush
26 pressure plate
27 bearing plate
28 load cell
29 spindle
30 electric motor
31 position sensor
32 guide rod
33 peak of curve
34 peak of curve
35 peak of curve
36 packer
37 cello-packer
38 pack conveyor
39 test station
40 intermediate conveyor
41 pack path
42 packaging unit
43 central computer
49A-D evaluation window

What is claimed is:

1. Method for the testing of cubio-shaped cigarette packs (10) of formable packaging material by impinging the pack (10) with a defined pressure created by lowering a pressure-exerting means (26) onto the pack (10) in a uniform motion and measuring the resulting deformations of the pack (10), comprising the steps of:
   a) during the deformation of the pack (10) by the pressure-exerting means (26), measuring (i) the distance covered by the pressure-exerting means (26) and (ii) using a measuring device (28) to determine the counterforce of the pack (10) exerted against the pressure-exerting means (26);
   b) determining a force versus distance diagram from the measured values of the distance and counterforce measured in step a); and
   c) comparing the force versus distance diagram with at least one additional force versus distance diagram for the same or a different pack (10).

2. Method according to claim 1, wherein the distance is measured by a position sensor (31) and the measuring device is a load cell (28).

3. Method according to claim 2, wherein the course of force acting on the pack (10) during uniform movement of the pressure-exerting means (26) is represented as a second derivative of the force versus distance diagram.

4. Method according to claim 3, wherein the pack (10) is a cuboid-shaped pack (10) comprising a large surface front side (13) and corresponding rear side and the force is transferred to the pack (10) across the entire pack surface on the entire large front side (13) or rear side.

5. Method according to claim 3, wherein the pressure-exerting means (26) is applied to the pack (10) at a constant rate of movement and the measuring device is a pressure gauge.

6. Method according to claim 2, wherein the measuring results of the load cell (28) and of the position sensor (31) are evaluated by a computer and plotted as a second derivative curve.

7. Method according to claim 2, wherein the pack (10) is a cuboid-shaped pack (10) comprising a large surface front side (13) and corresponding rear side and the force is transferred to the pack (10) across the entire pack surface on the entire large front side (13) or rear side.

8. Method according to claim 2, wherein the pressure-exerting means (26) is applied to the pack (10) at a constant rate of movement and the measuring device is a pressure gauge.

9. Method according to claim 1, further comprising the step of generating and displaying a graphic representation of force versus distance diagram, which shows the resistance force of the pack (10) as counterforce and which varies as the result of the increasing deformation of the pack (10) under uniform movement of the pressure-exerting means (26).

10. Method according to claim 9, wherein the graphic representation of the course of force acting on the pack (10) during its deformation is plotted as a curve, namely as the force applied to the pack (10) by the pressure-exerting means (26) over the distance traveled by the pressure-exerting means (26) acting on the pack (10).

11. Method according to claim 9, wherein the course of force acting on the pack (10) during uniform movement of the pressure exerting means (26) is represented as a second derivative of the force versus distance diagram.

12. Method according to claim 9, wherein the pack (10) is a cuboid-shaped pack (10) comprising a large surface front side (13) and corresponding rear side and the force is transferred to the pack (10) across the entire pack surface on the entire large front side (13) or rear side.

13. Method according to claim 9, wherein the pressure-exerting means (26) is applied to the pack (10) at a constant rate of movement and the measuring device is a pressure gauge.

14. Method according to claim 1, wherein the pack (10) is a cuboid-shaped pack (10) comprising a large surface front side (13) and corresponding rear side and the force is transferred to the pack (10) across the entire pack surface on the entire large front side (13) or rear side.

15. Method according to claim 14, wherein the pressure-exerting means (26) is applied to the pack (10) at a constant rate of movement and the measuring device is a pressure gauge.

16. Method according to claim 1, wherein the pressure-exerting means (26) is applied to the pack (10) at a constant rate of movement and the measuring device is a pressure gauge.

17. Apparatus for the testing of cigarette packs (10) of formable packaging material, in which the pack (10) is positioned between opposing pressure-exerting means, and in which at least one pressure-exerting means is movable against the pack (10), comprising:

a) a position sensor (31) arranged on the pressure-exerting means that is movable against the pack (10); and b) a load cell (28) arranged on the other pressure-exerting means, wherein the opposing pressure exerting means comprises an upper pressure plate (26) and a lower bearing plate (27), and the pressure plate (26) is mounted on a carrier that can be moved up and down on a pressure strut (24), which can be displaced by means of a uniformly driven gear mechanism.

18. Apparatus according to claim 17, further comprising a supporting framework with an upper traverse (22) and a lower traverse (23), which are connected to one another by supporting columns (20, 21); with the pressure strut (24) being displaceably mounted on the supporting columns (20, 21) and the load cell (28) positioned on the lower traverse (23).

19. Apparatus according to claim 18, wherein the position sensor (31) is attached to the displaceable pressure strut (24).

20. Apparatus according to claim 18, further comprising a test station (39) to which the apparatus, the test station being assigned to a packaging unit (42) for random testing of the packs (10).

21. Apparatus according to claim 17, wherein the position sensor (31) is attached to the displaceable pressure strut (24).

22. Apparatus according to claim 21, further comprising a test station (39) to which the apparatus, the test station being assigned to a packaging unit (42) for random testing of the packs (10).

23. Apparatus according to claim 17, further comprising a test station (39) to which the apparatus, the test station being assigned to a packaging unit (42) for random testing of the packs (10).

24. Apparatus according to claim 17, further comprising a test station (39) to which the apparatus, the test station being assigned to a packaging unit (42) for random testing of the packs (10).

25. Apparatus according to claim 24, wherein the test station (39) is positioned in the region of a pack conveyor (38) between a packer (36) and a cello-packer (37).

26. Apparatus according to claim 25, wherein a plurality of packaging units (42) having at least one test station (39) each are connected to a central computer (43) for the central logging of operational data concerning the testing results.

27. Apparatus according to claim 24, wherein a plurality of packaging units (42) having at least one test station (39) each are connected to a central computer (43) for the central logging of operational data concerning the testing results.

* * * * *

UNITED STATES PATENT AND TRADEMARK OFFICE
CERTIFICATE OF CORRECTION

PATENT NO. : 6,813,961 B2
DATED : November 9, 2004
INVENTOR(S) : Focke, Stiller, Schmidt, Sgodzai and Buse It is certified that error appears in the above-identified patent and that said Letters Patent is hereby corrected as shown below:

Title page,
Item [12], UNITED STATES PATENT, "Stiller et al." should be -- Focke et al. --.
Item [75], Inventors, should read, -- Heinz Focke, Verden (DE), Martin Stiller, Verden (DE), Jens Schmidt, Gradsberg (DE), Ralph Sgodzai, Ritterhude (DE), Henry Buse, Visselhovede (DE) --
Insert Item -- [30] Foreign Application Priority Data:
October 10, 2000 (DE) 10050297.0 --

Signed and Sealed this

Twelfth Day of July, 2005

JON W. DUDAS
*Director of the United States Patent and Trademark Office*